(12) United States Patent
Li et al.

(10) Patent No.: US 9,820,477 B2
(45) Date of Patent: Nov. 21, 2017

(54) METHOD AND SYSTEM FOR PREVENTING AND TREATING PESTS USING SMOKE FROM BIOMASS POWER PLANT

(71) Applicant: Zhongying Changjiang International New Energy Investment Co., Ltd., Wuhan (CN)

(72) Inventors: Wanli Li, Wuhan (CN); Jiangchuan Li, Wuhan (CN); Hao Gong, Wuhan (CN); Zhixiang Luo, Wuhan (CN)

(73) Assignee: ZHONGYING CHANGJIANG INTERNATIONAL NEW ENERGY INVESTMENT CO., LTD., Wuhan (CN)

( * ) Notice: Subject to any disclaimer, the term of this patent is extended or adjusted under 35 U.S.C. 154(b) by 392 days.

(21) Appl. No.: 14/324,148

(22) Filed: Jul. 4, 2014

(65) Prior Publication Data

US 2014/0317996 A1 Oct. 30, 2014

Related U.S. Application Data

(63) Continuation-in-part of application No. PCT/CN2012/087609, filed on Dec. 27, 2012.

(30) Foreign Application Priority Data

Jan. 5, 2012 (CN) .......................... 2012 1 0001912

(51) Int. Cl.
*A01M 1/20* (2006.01)
*A01M 13/00* (2006.01)
(Continued)

(52) U.S. Cl.
CPC ................ *A01M 1/20* (2013.01); *A01M 1/24* (2013.01); *A01M 13/00* (2013.01);
(Continued)

(58) Field of Classification Search
CPC .............. A01M 1/2022; A01M 1/2027; A01M 1/2066; A01M 1/2094; A01M 13/00; A01M 1/20
(Continued)

(56) References Cited

U.S. PATENT DOCUMENTS

| 3,348,922 A | * | 10/1967 | Bose | ........................ | A01G 9/18 |
| | | | | | 126/110 R |
| 3,999,329 A | * | 12/1976 | Brais | ...................... | A01G 9/246 |
| | | | | | 261/17 |
| 2005/0232810 A1 | * | 10/2005 | Yamamoto | ............ | A01M 13/00 |
| | | | | | 422/34 |

FOREIGN PATENT DOCUMENTS

| CN | 1425301 A | * | 6/2003 |
| CN | 102160505 A | * | 8/2011 |

OTHER PUBLICATIONS

English Translation of the Written Opinion of the International Search Authority—PCT/CN2012/087609, dated Apr. 4, 2013, 10 pages.*

* cited by examiner

*Primary Examiner* — Darren W Ark
*Assistant Examiner* — Danielle Clerkley
(74) *Attorney, Agent, or Firm* — Matthias Scholl P.C.; Matthias Scholl

(57) ABSTRACT

A method for pest control in a confined space using flue gas from a biomass power plant. The method includes: treating flue gas from a biomass power plant to yield treated flue gas having a volume concentration of carbon dioxide exceeding 85 volume %, and conducting pest control in a confined space according to the following steps: continuously aerating the confined space with the treated flue gas during a fallow period to allow a gas pressure in the confined space to reach between 0.110 and 0.140 megapascal of absolute (Continued)

pressure and the volume concentration of carbon dioxide in the confined space to reach between 50 and 90 volume %.

19 Claims, 1 Drawing Sheet

(51) Int. Cl.
 *A01N 59/04* (2006.01)
 *A01M 1/24* (2006.01)
 *B01D 53/047* (2006.01)
 *B01D 53/053* (2006.01)
(52) U.S. Cl.
 CPC .......... *A01M 13/003* (2013.01); *A01N 59/04* (2013.01); *B01D 53/047* (2013.01); *B01D 53/053* (2013.01); *B01D 2253/102* (2013.01); *B01D 2253/106* (2013.01); *B01D 2253/108* (2013.01); *B01D 2257/504* (2013.01); *B01D 2258/0283* (2013.01); *B01D 2259/404* (2013.01); *Y02C 10/08* (2013.01); *Y02P 60/24* (2015.11)
(58) Field of Classification Search
 USPC ...... 43/127, 129, 130; 47/1.01 R, 17, 58.1 R
 See application file for complete search history.

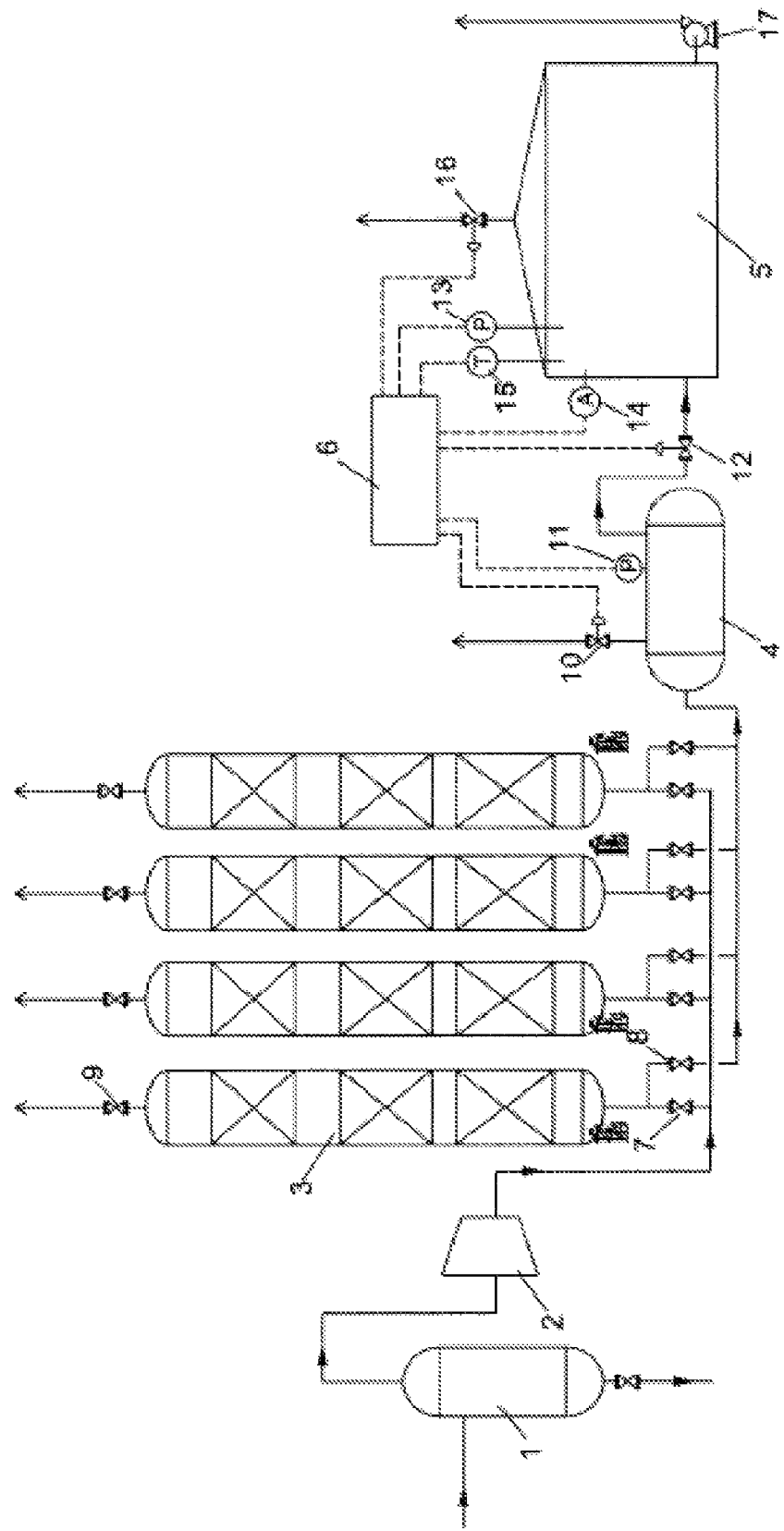

METHOD AND SYSTEM FOR PREVENTING AND TREATING PESTS USING SMOKE FROM BIOMASS POWER PLANT

CROSS-REFERENCE TO RELATED APPLICATIONS

This application is a continuation-in-part of International Patent Application No. PCT/CN2012/087609 with an international filing date of Dec. 27, 2012, designating the United States, now pending, and further claims priority benefits to Chinese Patent Application No. 201210001912.1 filed Jan. 5, 2012. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18$^{th}$ Floor, Cambridge, Mass. 02142.

BACKGROUND OF THE INVENTION

Field of the Invention

The invention relates to a method and a system for pest control in a confined space by using flue gas from a biomass power plant.

Description of the Related Art

Currently, biological pest control and physical pest control have no obvious effects, so that in confined space the chemical control is predominant. Long-term and extensive use of the chemical pesticide not only sharply increases the pesticide resistance of the pests and the diseases, but also results in environmental pollution. Meanwhile, cumulative amount of spores and hyphae of fungus and bacteria causing diseases, and eggs, pupae, and mature larva of the pest propagules significantly increases in the confined space.

Researches on the pest control using carbon dioxide have been carried out for a long time. Certain progresses in the pest control using carbon dioxide have been gained, and no drug resistance produced by pest control using carbon dioxide has been reported yet. However, the researches are still in laboratory stages, no explicit operation instruction has yet been disclosed, and the gas source is pure carbon dioxide, thereby having high production costs and being incapable for practical production and application.

Biomass power plant utilizes combustion of biomass in the presence of excessive air in a boiler for power generation. The produced hot flue gas exchanges heat with a heat exchanger of the boiler, and the produced high-temperature high-pressure steam does work while expanding in a steam turbine to generate power. The combusted biomass in the biomass power plant is mainly from wheat straws, corn stalks, straws, rice hulls, cotton stalks, and agricultural and forestry waste of forestry harvesting and processing residues, thereby featuring great resource, wide distribution, renewable, low pollution, no near emission of carbon dioxide. As species of the combusted biomass are different in different biomass power plants, the components in the flue gas are slightly different. Generally, the volume concentration of carbon dioxide in the flue gas discharged from a biomass power plant is approximately 14 volume %, and a content of pollutants including $SO_2$ is 50 ppm. Compared with the flue gas discharged from a thermal power plant, the content of pollutants including $SO_2$ is decreased by 85%, thereby being applicable for pest control.

SUMMARY OF THE INVENTION

Combining with current researches on the insect disinfestation and sterilization using carbon dioxide and on the basis of comprehensive utilization of flue gas from a biomass power plant, it is one objective of the invention to provide a method and a system for pest control in a confined space by using flue gas from a biomass power plant. The method is effective and safe in pest control and has good economic cycle benefits.

To achieve the above objective, in accordance with one embodiment of the invention, there is provided a method for pest control in a confined space by using flue gas from a biomass power plant, the method comprising: treating the flue gas from the biomass power plant to yield treated flue gas having a volume concentration of carbon dioxide of exceeding 85 v. %, and conducting pest control in the confined space using mode I, mode II, or a combination thereof.

mode I: continuously aerating the confined space with the treated flue gas during a fallow period to allow a gas pressure in the confined space to reach between 0.110 and 0.140 megapascal of absolute pressure and the volume concentration of carbon dioxide in the confined space to reach between 50 and 90 v. %, after a certain retention time, stopping aerating the confined space until the confined space returns to a normal state; and mode II: continuously aerating the confined space with the treated flue gas, when diseases and pests occur during the crops planting process, to allow a gas pressure in the confined space to reach between 0.110 and 0.140 megapascal of absolute pressure and the volume concentration of carbon dioxide in the confined space to reach between 50 and 90 v.%; controlling a time for each continuous introduction of the treated flue gas of between 15 and 60 min, stopping the introduction of the treated flue gas until the pressure returns normal and the volume concentration of carbon dioxide decreases to 5 v. % below; and repeating aerating the confined space with the treated flue gas after a certain interval.

In a class of this embodiment, the confined space is a greenhouse or a plastic house.

In a class of this embodiment, in mode I, the confined space is in a high-temperature stuffy period, a temperature in the confined space is between 40 and 75° C. The confined space is continuously aerated with the treated flue gas for between 8 and 12 days. A pressure in the confined space is between 0.110 and 0.120 megapascal of absolute pressure. The volume concentration of carbon dioxide in the confined space is between 80 and 90 volume %.

In a class of this embodiment, the interval for each treatment in mode II is controlled between 2 and 10 hours. The treatment is repeated for between 3 and 10 times. A temperature in the confined space is between 15 and 35° C.

In a class of this embodiment, the flue gas from the biomass power plant is treated with gas-liquid separation and pressure-swing absorption. An absorbent is a specific carbon dioxide selective absorbent, and an absorbing pressure is between 0.5 and 1.5 megapascal.

In a class of this embodiment, the specific carbon dioxide selective absorbent is silica gel, activated carbon, or a molecular sieve.

In a class of this embodiment, a pressure of the treated flue gas entering the confined space is between 0.30 and 0.50 megapascal, preferably 0.35 megapascal.

A system for pest control in a confined space using flue gas from a biomass power plant comprises: a flue gas treatment device, a storage tank of treated flue gas, and a control unit. A discharge pipe of the flue gas treatment device is connected to the storage tank of the treated flue gas, and the storage tank of the treated flue gas is connected to the confined space. A first regulating valve is disposed on a gas inlet pipe between the storage tank of the treated flue gas and the confined space. A first pressure monitoring sensor and a carbon dioxide concentration monitoring sensor are disposed inside the confined space, and a first atmospheric valve is disposed above the confined space. The control unit is connected to the first pressure monitoring sensor and the carbon dioxide concentration monitoring sensor for receiving detection signals therefrom. The control unit is connected to the first regulating valve and the first atmospheric valve for controlling opening degrees thereof, whereby regulating ranges of a pressure and a concentration of carbon dioxide in the confined space, respectively.

In a class of this embodiment, the flue gas treatment device comprises: a gas-liquid separation device, a gas compression device, and a pressure-swing absorption device. The pressure-swing absorption device adopts multibed swing pressure absorption and is formed by a parallel arrangement of a plurality of absorption towers. Each absorption tower is packed with a specific carbon dioxide selective absorbent. A top of each absorption tower is provided with a second atmospheric valve, and a bottom thereof is provided with two branch pipes functioning as a charging branch pipe and a discharging branch pipe of each absorption tower, respectively. Each charging branch pipe is provided with a charging regulating valve and all charging branch pipes are connected to form a charging main pipe. Each discharging branch pipe is provided with a discharging regulating valve and all discharging branch pipes are connected to form a discharging main pipe. A gas outlet of the gas-liquid separation device is connected to the gas compression device. The gas compression device is connected to the charging main pipe of the pressure-swing absorption device. The discharging main pipe of the pressure-swing absorption device is connected to the storage tank of the treated flue gas.

The pressure-swing absorption comprises the following steps: opening the charging regulating valve and the second atmospheric valve of each absorption tower, synchronously introducing the flue gas from the biomass power plant into a plurality of the absorption towers in absorption states to allow the flue gas to pass through absorbent bed layers from bottom to top and discharging gas out of the absorption tower to the atmosphere; when a front edge of the absorbed flue gas reaches an outlet of the absorption bed layer, closing the charging regulating valves and the second atmospheric valves of the pressure-swing absorption device to stop the charge of the flue gas and the absorption; opening the discharging regulating valve to introduce $CO_2$ after desorption in an opposite direction of the absorption to the storage tank of treated flue gas for storage; when the pressure in each absorption tower decreases to the normal pressure, introducing the flue gas from the biomass plant for sweeping so that absorbent in each absorption tower is completely regenerated, discharging the sweeping gas to the atmosphere, and gradually increasing the pressure to the absorption pressure and starting a next absorption cycle.

In a class of this embodiment, the storage tank of the treated flue gas is provided with a second pressure monitoring sensor. A second regulating valve is disposed above the storage tank of the treated flue gas. The control unit is connected to the second pressure monitoring sensor for receiving a detection signal therefrom and is connected to the second regulating valve for controlling a pressure at an outlet of the storage tank of the treated flue gas to reach a set pressure.

In a class of this embodiment, the confined space is further provided with a temperature monitoring sensor; and the temperature monitoring sensor is connected to the control unit for monitoring a temperature in the confined space.

In a class of this embodiment, a ventilation end of the confined space is connected to an induced draft fan for ventilation.

The flue gas from the biomass power plant is purified to obtain the treated flue gas having a high content of carbon dioxide and a low content of other harmful components. The treated flue gas is charged to the confined space in the fallow period or in occurrence of diseases and pests, so that residual propagules of various harmful organisms, such as fungal and bacterial spores, worm eggs, and pupae are safely and effectively eliminated, thereby actively facilitating the development of the green agriculture and the organic agriculture. In addition, the treated flue gas can be used in the confined space as a gas fertilizer during the plant growth by controlling the content of the carbon dioxide therein to improve the yield of the crops and further realize the comprehensive utilization of the flue gas from the biomass power plant. The pressure-swing absorption is adopted based on the characteristics of the absorbent that absorption capacity of the absorbent on different gases varies along with the change of the pressure. Carbon dioxide is absorbed during the increase of the pressure and is desorbed during the decrease of the pressure, while other weakly absorbed ingredients pass through the absorption bed layers. Thus, carbon dioxide in the flue gas from the biomass power plant is concentrated, and the content of the harmful components like $SO_2$ in the flue gas is further decreased.

Advantages of the invention are summarized as follows:

1. The method for pest control in the confined space by using the flue gas from the biomass power plant has a simple process, good effect, safe control, no drug resistance, and no residue.

2. The flue gas from the biomass power plant is used as the raw material for the pest control, so that the method has economic cycle, good benefits, and convenience for wide application.

3. The automatic control is realized and the operation is simple.

BRIEF DESCRIPTION OF THE DRAWINGS

The invention is described hereinbelow with reference to accompanying drawings, in which the sole FIGURE is a structure diagram of a system for pest control in a confined space by using flue gas from a biomass power plant.

In the drawings, the following numbers are used: 1. Gas-liquid separator; 2. Compressor; 3. Pressure-swing absorption device; 4. Storage tank of treated flue gas; 5. Confined space; 6. Control unit; 7. Charging regulating valve; 8. Discharging regulating valve; 9. Second atmospheric valve; 10. Second regulating valve; 11. Second pressure monitoring sensor; 12. Air inlet regulating valve; 13. First pressure monitoring sensor; 14. Carbon dioxide concentration monitoring sensor; 15. Temperature monitoring sensor; 16. First atmospheric valve; and 17. Induced draft fan.

DETAILED DESCRIPTION OF THE EMBODIMENTS

For further illustrating the invention, experiments detailing a method and a system for pest control in a confined space by using flue gas from a biomass power plant are described below. It should be noted that the following examples are intended to describe and not to limit the invention.

Pests herein are not particularly limited and comprise propagules of insects, arthropods, nematodes, fungus, bacteria that endanger farm crops. For example, spores and mycelium of fungus and bacteria causing grey mold, sclerotia, blight, leaf mold, and downy mildew, and eggs and pupae of pest propagules of aphid, whitefly (*Bemisia tabaci*), diamondback moth (*Plutella xylostella*), noctuid, and nematodes.

Specific experiments are conducted as follows:

Experimental plots having corresponding history records of pest occurrence are selected. Crops are planted in confined spaces like a plastic house or a greenhouse. The experimental crops are treated by flue gas as a flue gas treatment group, by chemical control as a control treatment group, respectively. Experimental crops planted in another experimental plot are conducted with no pest control treatment and are used as a blank control group. Pest and disease control rate is calculated using the following equations:

Pest control rate (%)=[1−(pest number/pest number in the blank control group)]×100; and Disease control rate (%)=[1−(disease index/disease index in the blank control group)]×100.

EXAMPLE 1

Experimental plot: an experimental plot where the occurrence of the diamondback moth was serious in the history.

Experimental crops: cabbages (*Brassica oleracea* var. *capitata*), planted in the greenhouse.

The flue gas treatment group:

A system for pest control in a confined space by using flue gas from a biomass power plant comprises: a gas-liquid separator 1, a compressor 2, a pressure-swing absorption device 3, a storage tank for treated flue gas 4, and a control unit 6. The pressure-swing absorption device comprises a plurality of absorption towers in parallel arrangement. Each absorption tower is packed with a molecular sieve of a specific carbon dioxide selective absorbent. A top of each absorption tower is provided with a second atmospheric valve 9, and a bottom thereof is provided with two branch pipes functioning as a charging branch pipe and a discharging branch pipe of each absorption tower, respectively. Each charging branch pipe is provided with a charging regulating valve 7 and all charging branch pipes are connected to form a charging main pipe. Each discharging branch pipe is provided with a discharging regulating valve 8 and all discharging branch pipes are connected to form a discharging main pipe. A gas outlet of the gas-liquid separator 1 is connected to a gas outlet of the compressor device 2. The compressor is connected to the charging main pipe of the pressure-swing absorption device 3. The discharging main pipe of the pressure-swing absorption device is connected to the storage tank 4 of the treated flue gas. The storage tank of the treated flue gas is connected to the confined space 5. A first regulating valve 12 is disposed on a gas inlet pipe between the storage tank of the treated flue gas and the confined space. A first pressure monitoring sensor 13 and a carbon dioxide concentration monitoring sensor 14 are disposed in an upper part inside the confined space, and a first atmospheric valve is disposed above the confined space. The control unit 6 is connected to the first pressure monitoring sensor and the carbon dioxide concentration monitoring sensor for receiving detection signals therefrom. The control unit is connected to the first regulating valve and the first atmospheric valve for controlling opening degrees thereof, whereby regulating ranges of a pressure and a concentration of carbon dioxide in the confined space, respectively. A ventilation end of the confined space is connected to an induced draft fan for ventilation. The storage tank of the treated flue gas is provided with a second pressure monitoring sensor 11 and a second regulating valve 10. The control unit is connected to the second pressure monitoring sensor for receiving a detection signal therefrom and is connected to the second regulating valve for controlling a pressure at an outlet of the storage tank of the treated flue gas, that is, a pressure of the treated flue gas entering the confined space, to reach a set pressure. A temperature monitoring sensor 15 is disposed in an upper part inside the confined space. The temperature monitoring sensor is connected to the control unit for monitoring a temperature in the confined space. The confined space is the greenhouse.

In the above system, the flue gas from the biomass power plant having a temperature of 140° C. and a $CO_2$ content of 14 v. % flows through the gas-liquid separator for separation, through the compressor and to the pressure-swing absorption device for treatment. The treatment in the pressure-swing absorption device is conducted as follows: the charging regulating valve and the second atmospheric valve of each absorption tower are opened, the flue gas from the biomass power plant is synchronously introduced into four absorption towers in absorption states to allow the flue gas to pass through absorbent bed layers from bottom to top and gas flowing out of the absorption tower is discharged to the atmosphere. When a front edge of the absorbed flue gas reaches an outlet of the absorption bed layer, the charging regulating valves and the second atmospheric valves of the pressure-swing absorption device are closed to stop the introduction of the flue gas so that the absorption is correspondingly stopped. The discharging regulating valve is opened to discharge $CO_2$ after desorption in an opposite direction of the absorption to the storage tank of treated flue gas for storing the treated flue gas having the concentration of carbon dioxide of 96 v. %. When the pressure in each absorption tower decreases to the normal pressure, the flue gas from the biomass plant is introduced for sweeping so that the absorbent in each absorption tower is completely regenerated, and the sweeping gas is discharged to the atmosphere. Thereafter, the pressure is gradually increased to the absorption pressure to start a next absorption cycle.

The pressure of the treated flue gas at the outlet of the storage tank of the treated flue gas, that is, the pressure of the treated flue gas entering the confined space, is controlled at 0.35 megapascal, by using the second pressure monitoring sensor to monitor the pressure at the outlet of the tank of the treated flue gas and using the control unit to control the opening degree of the second regulating valve. The treated flue gas is introduced to the greenhouse before plantation of cabbages in a stuffy period. The first pressure monitoring sensor and the carbon dioxide concentration sensor are utilized to detect the pressure and the concentration of carbon dioxide in the plastic house, respectively, and the control unit is used to control opening degrees of the first regulating valve and the first atmospheric valve so that the pressure in the plastic house is controlled to be 0.120 megapascal of absolute pressure, the volume concentration of carbon dioxide is controlled to be 80 v. %, and the temperature in the plastic house monitored by the temperature monitoring sensor is 65° C. The above parameters are maintained for 8 days. Thereafter, the introduction of the treated flue gas is stopped, the ventilation end of the confined space is opened for ventilation for between 1 and 3 days until the volume concentration of carbon dioxide returns to the normal state (0.03 v. %) and the temperature returns to the room temperature. During the ventilation process, the induced draft fan is utilized to realize fast ventilation if necessary. After that, cabbages are planted. In a rosette stage and a heading stage of the growth of the cabbage, the confined space is continuously aerated with the treated flue gas from the storage tank and the treatment is repeated after a certain interval. Meanwhile, by using the first pressure monitoring sensor and the carbon dioxide concentration sensor to detect the pressure and the concentration of carbon dioxide in the plastic house, respectively, and by using the control unit to control the opening degrees of the first regulating valve and the first atmospheric valve, the gas pressure in the confined space reaches 0.115 megapascal of absolute pressure, the volume concentration of carbon dioxide reaches 80 v. %, and the temperature in the plastic house, monitored by the temperature monitoring sensor, is 25° C. After 15 minutes of each continuous introduction of the treated flue gas. The confined space is ventilated until the pressure therein returns normal and the volume concentration of carbon dioxide therein decreases to 5 volume % below. The above treatment is repeated for 10 times at the interval of 5 hours.

The control treatment group: 1000 times liquid of *Bacillus thuringiensis* is sprayed for once and 1000 times liquid of Avermectins is sprayed for twice during a seedling stage of the cabbages. 1000 times liquid of 5% flufenoxuron is sprayed during the rosette stage, and 800 times liquid of 25% chlorbenzuron is sprayed for once in the heading stage.

The blank control group: no control treatment is conducted.

In harvest period of the cabbages, 20 samples are respectively collected from the above three groups using a checkerboard method, the number of larvae of the diamondback moths are counted, and pest control rates are calculated, respectively, specific results of which are shown in Table 1.

TABLE 1

| Objects to be controlled | | Times of pesticide application | Control rate |
|---|---|---|---|
| Diamondback moth | Treatment group | 0 | 95.7% |
| | Control group | 5 | 86.9% |
| Flea beetle | Treatment group | 0 | 98.5% |
| | Control group | 2 | 92.4% |
| Noctuid | Treatment group | 0 | 94.5% |
| | Control group | 4 | 84.2% |
| *Meloidogyne incongnita* | Treatment group | 0 | 99.1% |
| | Control group | 3 | 81.2% |
| Damping-off of tomato | Treatment group | 0 | 92.3% |
| | Control group | 2 | 81.4% |
| Bacterial blight of *anthurium* | Treatment group | 0 | 94.5% |
| | Control group | 3 | 82.3% |

EXAMPLE 2

Experimental plot: an experimental plot where the occurrence of the flea beetle was serious in the history.

Experimental crops: radish (*Raphanus sativus*), planted in the greenhouse.

The flue gas treatment group:

The system for the pest control in the confined space in Example 1 is used to treat the flue gas from the biomass power plant and is specifically conducted as follows:

Before the plantation of the radishes, the greenhouse is continuously aerated with the treated flue gas having a volume concentration of carbon dioxide of exceeding 96 volume % from the storage tank during the stuffy period. The pressure in the greenhouse is controlled at 0.130 megapascal and the volume concentration of carbon dioxide therein is controlled at 85 volume %. The temperature monitored by the temperature monitoring sensor is at 70° C. After maintenance for 10 days, the introduction of the flue gas is stopped until the temperature and the pressure in the greenhouse return to normal states. After that, radishes are planted. In a growing period of fleshy root of the radishes, the confined space is continuously aerated with the treated flue gas from the storage tank to repeat the treatment after a certain interval and to allow the pressure therein to reach 0.115 megapascal of absolute pressure, the volume concentration of carbon dioxide therein to reach 70 volume %, and a temperature monitored by the temperature monitoring sensor to reach 20° C. during each treatment. After 18 minutes of each treatment, the confined space is ventilated until the pressure therein returns normal and the volume concentration of carbon dioxide therein decreases to 5 volume % below. The above treatment is repeated for 5 times at the interval of 10 hours.

The control treatment group: 800 times liquid of imidacloprid 10% water dispersible powder (WP) is applied for once during a seedling stage of the radishes, and 800 times liquid of 20% chlorpyrifos is applied during a swelling period.

The blank control group: no control treatment is conducted.

In harvest period of the radishes, 30 samples are respectively collected from the above three groups using a checkerboard method, the number of larvae and adults of the flea beetles are counted, and pest control rates are calculated, respectively, specific results of which are shown in Table 1.

EXAMPLE 3

Experimental plot: an experimental plot where the occurrence of the noctuid was serious in the history.

Experimental crops: mustard (*Brassica juncea*), planted in the greenhouse.

The flue gas treatment group:

The system for the pest control in the confined space in Example 1 is used to treat the flue gas from the biomass power plant and is specifically conducted as follows:

Before the plantation of the mustards, the greenhouse is continuously aerated with the treated flue gas having a volume concentration of carbon dioxide of exceeding 96 volume % from the storage tank during the stuffy period. The pressure in the greenhouse is controlled at 0.126 megapascal and the volume concentration of carbon dioxide therein is controlled at 80 volume %. The temperature monitored by the temperature monitoring sensor is at 70° C. After maintenance for 9 days, the introduction of the flue gas is stopped until the temperature and the pressure in the greenhouse return to normal states. After that, mustards are planted. In a vegetative period of the mustards, the confined space is continuously aerated with the treated flue gas from the storage tank to repeat the treatment after a certain interval and to allow the pressure therein to reach 0.125 megapascal of absolute pressure, the volume concentration of carbon dioxide therein to reach 85 volume %, and a temperature monitored by the temperature monitoring sensor to reach 30° C. during each treatment. After 15 minutes of each treatment, the confined space is ventilated until the pressure therein returns normal and the volume concentration of carbon dioxide therein decreases to 5 volume % below. The above treatment is repeated for 7 times at the interval of 6 hours.

The control treatment group: 800 times liquid of 48% lesiben and 800 times liquid of 5% fipronil are applied for once, respectively, during a seedling stage of the mustards, and 10% Cypermethrin and Fenvalerate EC are applied for once, respectively, during the vegetative period.

The blank control group: no control treatment is conducted.

In harvest period of the mustards, 30 samples are respectively collected from the above three groups using a checkerboard method, the number of larvae of the noctuid are counted, and pest control rates are calculated, respectively, specific results of which are shown in Table 1.

EXAMPLE 4

Experimental plot: an experimental plot where the occurrence of *Meloidogyne incongnita* was serious in the history.

Experimental crops: cucumber (*Cucumis sativus*), planted in the plastic house.

The flue gas treatment group:

The system for the pest control in the confined space in Example 1 is used to treat the flue gas from the biomass power plant and is specifically conducted as follows:

Before the plantation of the cucumbers, the plastic house is continuously aerated with the treated flue gas having a volume concentration of carbon dioxide of exceeding 96 volume % from the storage tank during the stuffy period. The pressure in the plastic house is controlled at 0.115 megapascal and the volume concentration of carbon dioxide therein is controlled at 80 volume %. The temperature monitored by the temperature monitoring sensor is at 50° C. After maintenance for 11 days, the introduction of the flue gas is stopped until the temperature and the pressure in the plastic house return to normal states. After that, cucumbers are planted. In a pick fruit stage of the mustards, the confined space is continuously aerated with the treated flue gas from the storage tank to repeat the treatment after a certain interval and to allow the pressure therein to reach 0.115 megapascal of absolute pressure, the volume concentration of carbon dioxide therein to reach 80 volume %, and a temperature monitored by the temperature monitoring sensor to reach 20° C. during each treatment. After 30 minutes of each treatment, the confined space is ventilated until the pressure therein returns normal and the volume concentration of carbon dioxide therein decreases to 5 volume % below. The above treatment is repeated for 8 times at the interval of 8 hours.

The control treatment group: 800 times liquid of Avermectin is applied for once and 500 times liquid of Aluopaizi is applied for twice during a seedling stage of the cucumbers.

In harvest period of the cucumbers, 20 samples are respectively collected from the above three groups using a checkerboard method, the number of root knots and the egg spawns (equivalent to the number of the worms) are counted, and disease control rates are calculated, respectively, specific results of which are shown in Table 1.

EXAMPLE 5

Experimental plot: an experimental plot where the occurrence of damping-off of tomato was serious in the history.

Experimental crops: tomato (*Lycopersicon esculentum*), planted in the greenhouse.

The flue gas treatment group:

The system for the pest control in the confined space in Example 1 is used to treat the flue gas from the biomass power plant and is specifically conducted as follows:

Before the plantation of the tomatoes, the greenhouse is continuously aerated with the treated flue gas having a volume concentration of carbon dioxide of exceeding 96 volume % from the storage tank during the stuffy period. The pressure in the greenhouse is controlled at 0.128 megapascal and the volume concentration of carbon dioxide therein is controlled at 85 volume %. The temperature monitored by the temperature monitoring sensor is at 70° C. After maintenance for 11 days, the introduction of the flue gas is stopped until the temperature and the pressure in the greenhouse return to normal states. After that, tomatoes are planted. In a seedling stage and a blooming stage of the tomatoes, the confined space is continuously aerated with the treated flue gas from the storage tank to repeat the treatment after a certain interval and to allow the pressure therein to reach 0.130 megapascal of absolute pressure, the volume concentration of carbon dioxide therein to reach 85 volume %, and a temperature monitored by the temperature monitoring sensor to reach 20° C. during each treatment. After 25 minutes of each treatment, the confined space is ventilated until the pressure therein returns normal and the volume concentration of carbon dioxide therein decreases to 5 volume % below. The above treatment is repeated for 2 times at the interval of 8 hours.

The control treatment group: 600 times liquid of 60% carbendazim is used for seed dressing before sowing seeds. 700 times liquid of 4% tolclofos-methyl is applied for once during a seedling stage, and dihydrogen phosphate phytoalexin is applied for once during a fruit swelling stage.

The blank control group: no control treatment is conducted.

In harvest period of the tomatoes, 20 samples are respectively collected from the above three groups using a checkerboard method for investigating the damping-off lesions, the disease incidence of the three groups are calculated, and disease control rates are calculated, respectively, specific results of which are shown in Table 1.

EXAMPLE 6

Experimental plot: an experimental plot where the occurrence of bacterial blight of anthurium was serious in the history.

Experimental crops: planting flowers anthurium, planted in the greenhouse.

The flue gas treatment group:

The system for the pest control in the confined space in Example 1 is used to treat the flue gas from the biomass power plant and is specifically conducted as follows:

Before the plantation of anthuriums, the greenhouse is continuously aerated with the treated flue gas from the storage tank during the stuffy period. The pressure in the greenhouse is controlled at 0.115 megapascal and the volume concentration of carbon dioxide therein is controlled at 70 volume %. The temperature monitored by the temperature monitoring sensor is at 66° C. After maintenance for 10 days, the introduction of the flue gas is stopped until the temperature and the pressure in the greenhouse return to normal states. After that, the anthuriums are planted. In an early blooming period of the anthuriums, the confined space is continuously aerated with the treated flue gas from the storage tank to repeat the treatment after a certain interval and to allow the pressure therein to reach 0.115 megapascal of absolute pressure, the volume concentration of carbon dioxide therein to reach 80 volume %, and a temperature monitored by the temperature monitoring sensor to reach 20° C. during each treatment. After 20 minutes of each treatment, the confined space is ventilated until the pressure therein returns normal and the volume concentration of carbon dioxide therein decreases to 5 volume % below. The above treatment is repeated for 8 times at the interval of 10 hours.

The control treatment group: 200 ppm of streptomycin and 200 ppm of oxytetracycline are applied for twice in a seedling stage of the anthuriums, and 200 ppm of streptomycin and 200 ppm of oxytetracycline are applied for twice in a bud stage of the anthuriums.

The blank control group: no control treatment is conducted.

During a best view period of the anthuriums, 20 samples are respectively collected from the above three groups using a checkerboard method for investigating the blight lesions, the disease incidence of the three groups are calculated, and disease control rates are calculated, respectively, specific results of which are shown in Table 1.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for pest control in a confined space having an original temperature and an original pressure using flue gas from a biomass power plant, the method, in sequence, comprising:
   step 1) treating flue gas from a biomass power plant to yield treated flue gas having a volume concentration of carbon dioxide of exceeding 85 vol. %;
   step 2) during a fallow period, continuously aerating the confined space with the treated flue gas to allow a gas pressure in the confined space to reach between 0.110 and 0.140 megapascal of absolute pressure and the volume concentration of carbon dioxide in the confined space to reach between 50 and 90 vol. %; and
   step 3) stopping aerating the confined space until a final temperature and a final pressure in the confined space equal the original temperature and the original pressure, respectively.

2. The method of claim 1, wherein the confined space is a greenhouse or a plastic house.

3. The method of claim 1, wherein in step 2):
   a temperature of the confined space is between 40 and 75° C.;
   the confined space is continuously aerated with the treated flue gas for between 8 and 12 days;
   the gas pressure in the confined space is between 0.110 and 0.120 megapascal of absolute pressure; and
   the volume concentration of carbon dioxide in the confined space is between 80 and 90 vol. %.

4. The method of claim 1, wherein the flue gas from the biomass power plant is treated with gas-liquid separation and pressure-swing absorption; an absorbent is a specific carbon dioxide selective absorbent, and an absorbing pressure is between 0.5 and 1.5 megapascal.

5. The method of claim 4, wherein the specific carbon dioxide selective absorbent is silica gel, activated carbon, or a molecular sieve.

6. The method of claim 1, wherein a pressure of the treated flue gas entering the confined space is between 0.30 and 0.50 megapascal.

7. A method for pest control in a confined space having an original pressure, the method, in sequence, comprising:
   step 1) treating flue gas from a biomass power plant to yield treated flue gas having a volume concentration of carbon dioxide of exceeding 85 vol. %;
   step 2) during a crop planting process, continuously aerating the confined space with the treated flue gas to allow a gas pressure in the confined space to reach between 0.110 and 0.140 megapascal of absolute pressure and a volume concentration of carbon dioxide in the confined space to reach between 50 and 90 vol. %, controlling a time for the introduction of the treated flue gas of between 15 and 60 min, stopping the introduction of the treated flue gas until a final pressure in the confined space equals the original pressure and the volume concentration of carbon dioxide in the confined space decreases to 5 vol. % below; and
   step 3) repeating step 2).

8. The method of claim 7, wherein the confined space is a greenhouse or a plastic house.

9. The method of claim 7, wherein step 2) is repeated for between 3 and 10 times at a time interval of between 2 and 10 hours; and in step 2), a temperature in the confined space is between 15 and 35° C.

10. The method of claim 7, wherein the flue gas from the biomass power plant is treated with gas-liquid separation and pressure-swing absorption; an absorbent is a specific carbon dioxide selective absorbent, and an absorbing pressure is between 0.5 and 1.5 megapascal.

11. The method of claim 10, wherein the specific carbon dioxide selective absorbent is silica gel, activated carbon, or a molecular sieve.

12. The method of claim 7, wherein a pressure of the treated flue gas entering the confined space is between 0.30 and 0.50 megapascal.

13. A method for pest control in a confined space having an original temperature and an original pressure, the method, in sequence, comprising:
   step 1) treating flue gas from a biomass power plant to yield treated flue gas having a volume concentration of carbon dioxide of exceeding 85 vol. %;
   step 2) during a fallow period, continuously aerating the confined space with the treated flue gas to allow a gas pressure in the confined space to reach between 0.110 and 0.140 megapascal of absolute pressure and a volume concentration of carbon dioxide in the confined space to reach between 50 and 90 vol. %, and stopping aerating the confined space until a final temperature and a final pressure in the confined space equal the original temperature and the original pressure, respectively;
   step 3) during a crop planting process, continuously aerating the confined space with the treated flue gas to allow the gas pressure in the confined space to reach between 0.110 and 0.140 megapascal of absolute pressure and the volume concentration of carbon dioxide in the confined space to reach between 50 and 90 vol. %, controlling a time for the introduction of the treated flue gas of between 15 and 60 min, stopping the introduction of the treated flue gas until the final pressure in the confined space equals the original pressure and the volume concentration of carbon dioxide in the confined space decreases to 5 vol. % below; and step 4) repeating step 3).

14. The method of claim 13, wherein the confined space is a greenhouse or a plastic house.

15. The method of claim 13, wherein in step 2):

a temperature of the confined space is between 40 and 75° C.;

the confined space is continuously aerated with the treated flue gas for between 8 and 12 days;

the gas pressure in the confined space is between 0.110 and 0.120 megapascal of absolute pressure; and the volume concentration of carbon dioxide in the confined space is between 80 and 90 vol. %.

16. The method of claim 13, wherein step 3) is repeated for between 3 and 10 times at a time interval of between 2 and 10 hours; and in step 3), a temperature in the confined space is between 15 and 35° C.

17. The method of claim 13, wherein the flue gas from the biomass power plant is treated with gas-liquid separation and pressure-swing absorption; an absorbent is a specific carbon dioxide selective absorbent, and an absorbing pressure is between 0.5 and 1.5 megapascal.

18. The method of claim 17, wherein the specific carbon dioxide selective absorbent is silica gel, activated carbon, or a molecular sieve.

19. The method of claim 13, wherein a pressure of the treated flue gas entering the confined space is between 0.30 and 0.50 megapascal.

\* \* \* \* \*